US009855557B2

(12) United States Patent
Thorne et al.

(10) Patent No.: US 9,855,557 B2
(45) Date of Patent: Jan. 2, 2018

(54) MICROPLATES AND METHODS FOR PROTEIN CRYSTALLIZATION AND BIOTECHNOLOGY

(71) Applicant: MITEGEN, LLC, Ithaca, NY (US)

(72) Inventors: Robert E. Thorne, Ithaca, NY (US); Benjamin Apker, Barton, NY (US); Robert Newman, Ithaca, NY (US)

(73) Assignee: MITEGEN, LLC, Ithaca, NY (US)

( * ) Notice: Subject to any disclaimer, the term of this patent is extended or adjusted under 35 U.S.C. 154(b) by 0 days.

(21) Appl. No.: 14/385,573

(22) PCT Filed: Mar. 28, 2013

(86) PCT No.: PCT/US2013/034251
§ 371 (c)(1),
(2) Date: Sep. 16, 2014

(87) PCT Pub. No.: WO2013/148938
PCT Pub. Date: Oct. 3, 2013

(65) Prior Publication Data
US 2015/0093306 A1    Apr. 2, 2015

Related U.S. Application Data

(60) Provisional application No. 61/617,102, filed on Mar. 29, 2012.

(51) Int. Cl.
*B01L 3/00*    (2006.01)
*C30B 35/00*    (2006.01)
*C12M 1/32*    (2006.01)

(52) U.S. Cl.
CPC .......... *B01L 3/5085* (2013.01); *C12M 23/12* (2013.01); *C30B 35/002* (2013.01); *B01L 2200/0678* (2013.01); *B01L 2300/0829* (2013.01); *B01L 2300/0858* (2013.01); *B01L 2300/0893* (2013.01)

(58) Field of Classification Search
CPC ..... B01L 3/5085; C30B 35/002; C12M 23/12
USPC ....................................................... 422/552
See application file for complete search history.

(56) References Cited

U.S. PATENT DOCUMENTS

| 6,913,732 | B2 * | 7/2005 | Sha et al. ................ 422/553 |
| 7,514,043 | B2 * | 4/2009 | Viola et al. .............. 422/534 |
| 2003/0027225 | A1 * | 2/2003 | Wada et al. ............. 435/7.21 |
| 2003/0150379 | A1 * | 8/2003 | Goodwin, Jr. ........... 117/204 |
| 2004/0259091 | A1 * | 12/2004 | Yasuda et al. .............. 435/6 |

(Continued)

OTHER PUBLICATIONS

International Search Report Form PCT/ISA/220, International Application No. PCT/US 2013/034251, dated Jul. 22, 2013, pp. 1-11.

*Primary Examiner* — Jill Warden
*Assistant Examiner* — Jacqueline Brazin
(74) *Attorney, Agent, or Firm* — Bond, Schoeneck & King, PLLC; William Greener; Frederick Price

(57) ABSTRACT

Devices and methods for manual and high-throughput protein crystal growth and growth of other biological and organic crystals. A microplate includes a plurality of cells and a frame that defines the cells in the microplate. In each cell there is at least one well open at top. Each well in a cell may be enclosed at bottom, or it may be open at bottom, in which case the well bottom may be sealed by a separate part, which may be, e.g., a separate film or plate (e.g., of plastic, glass or metal) or a molded part.

19 Claims, 8 Drawing Sheets

(56) References Cited

U.S. PATENT DOCUMENTS

2007/0202538 A1    8/2007   Glezer et al.
2009/0111711 A1    4/2009   Lewandowski et al.
2009/0255601 A1*   10/2009   Baeuerle et al. ............. 137/892

* cited by examiner (a)

(b)

(c)

(a)

(b)

(c)

(a)  (b)  (c)  (d)

MICROPLATES AND METHODS FOR PROTEIN CRYSTALLIZATION AND BIOTECHNOLOGY

REFERENCE TO RELATED APPLICATIONS

The instant application claims priority to U.S. provisional application Ser. No. 61/617,102 filed on Mar. 29, 2012, the subject matter of which is incorporated by reference herein.

The invention pertains to the field of biotechnology. More particularly, the invention pertains to improvements to microplates, including those used for protein crystal growth.

Many fields of bioscience and biotechnology use microplates for screening and other experiments. Microplates generally consist of a large number (e.g., 24, 96, 386, 1536) of identical cells arranged in a regular (usually rectangular) array. Each cell contains one or more wells or reservoirs into which liquids or other samples of interest are dispensed. The microplates are generally made by injection molding plastic. After dispensing samples into the wells, the top of the microplate is often sealed to protect the experiment from the environment. Most microplate designs conform to ANSI standards established by the Society for Biomolecular Sciences (SBS).

A specific application of microplates is in the fields of structural biology and X-ray crystallography, where they are used to grow crystals of proteins, nucleic acids, viruses, and other biomacromolecular complexes, and to explore the solubility of proteins in different solutions. Obtaining crystals of suitable size and quality for X-ray diffraction studies remains an important bottleneck in determining structures of biological macromolecules. Solution conditions (pH, salt type and concentration, protein concentration, concentrations of cryoprotectants and other additives) that yield crystal growth must be identified, and then optimized to yield crystals with adequate diffraction resolution for structure determination.

FIG. 1 shows a typical protein crystallization microplate, and FIG. 1(c) shows a typical cell in such a microplate. Each cell in the microplate generally has one or more small wells for protein solution and a larger well for the "reservoir" solution.

Vapor diffusion is the most common method for growing crystals of proteins, viruses and biomolecular assemblies, as well as of small molecule compounds that may be useful as drugs. In vapor diffusion growth, each reservoir well is filled with a protein-free solution, and a drop of protein solution is deposited on the bottom of one of the smaller wells. The microplate (and thus each cell) is then sealed using a plastic film. Typical volumes of reservoir solution are 20-200 microliters, and typical volumes of protein solution are 0.2-2 microliters. The air spaces above the reservoir and protein wells, within any given cell, are open to each other, allowing vapor to flow between them. The reservoir solution initially has a lower water vapor pressure than the protein drop. Water evaporates from the protein drop and condenses in the reservoir until the vapor pressures reach equilibrium. Water evaporation from the protein drop gradually increases the protein concentration in the protein drop. In favorable circumstances, this leads to crystal nucleation and growth.

Some manufacturers of plates for protein crystallization include Greiner Bio-One International (Austria), Corning (Corning, N.Y.), Art Robbins Instruments (Sunnyvale, Calif.), Hampton Research (Aliso Viejo, Calif.), Neuroprobe (Gaithersburg, Md.) and TTP LabTech (UK). Together, more than 200 different designs for crystallization plates are available.

Other approaches to high-throughput protein crystallization are being pursued. For example, Fluidigm (San Francisco, Calif.) and Emerald Biosystems (Bainbridge, Wash.) have commercialized platforms based on microfluidic chips. Although these allow crystallization with very small volumes, the chips are expensive compared with conventional microplates, they require specialized and very expensive hardware for loading, and the chip-hardware combination provides less flexibility in design of crystallization experiments. They are also incompatible with the SBS standards.

An important direction in recent years has been the development of methods for examining crystals using X-rays without removing the crystals from the plate or device in which they are grown. Drops have been dispensed into nylon loops, onto thin films, or into X-ray transparent glass capillaries, and the crystals that have grown have been examined by directing X-rays through the film, loop or capillary without removing the crystals. Oxford Diffraction (since acquired by Agilent) developed a special X-ray machine with a vertical X-ray beam for examining crystals in conventional SBS microplates. Greiner Bio-One in collaboration with NatXray (France) has developed microplates with thin (250 micrometer) windows to reduce background scattering in such applications.

Problems with Current Microplate Technology

Microplates are held in a horizontal orientation during liquid dispensing and routine use. If current protein crystallization microplates are rotated toward the vertical or if they are inverted, within each cell the contents of the wells will spill out and mix. Similarly, mixing can occur if the plates experience sharp accelerations. Mixing corrupts experiments. In the case of protein crystallization, early mixing of reservoir and protein solutions can lead to abrupt precipitation or to nucleation and growth of very large numbers of unsuitably small crystals. Consequently, most current microplates must be kept near the horizontal and handled very gently.

This handling restriction limits the usefulness of current plates, for several reasons.

First, since current microplates cannot be inverted, crystallization can only be performed in the "sitting drop" configuration. Under the influence of gravity, crystals that nucleate within the protein drop will sediment onto the supporting surface. Often they adhere to this surface, making retrieval difficult. If the plates could be inverted to the "hanging drop" configuration, crystals would sediment to the drop-air interface, from which they could be easily harvested for subsequent study.

Second, since plates cannot easily be rotated to the vertical without the danger of mixing well contents, inspection of each cell using X-rays and other electromagnetic probes is much more difficult. Nearly all X-ray sources used in crystallography—including tube and rotating anode lab sources and synchrotron sources—produce horizontal X-ray beams, so that plates must be rotated to the vertical for X-ray inspection of the contents of each cell. Infrared and UV spectrometry are also typically performed using horizontal illumination. In protein crystallization, the protein drops often contain precipitate and salt crystals and are often covered by "skins" formed from polyethylene glycols or denatured protein. Visually identifying crystalline protein, especially when the crystals are only microns in size, can be extremely difficult. In situ inspection using X-rays provides the most reliable crystal detection and assessment of crystal quality.

Third, with sufficiently X-ray transparent plate materials, in favorable cases X-ray crystallography and structure determination can be performed in situ, on a crystal residing in the plate. However, this in general requires that the crystal and thus the plate be rotated by typically 60 or 90 degrees about axes perpendicular to the X-ray beam. This is feasible with current plates only for crystals with certain orientations.

Fourth, in almost any non-automated handling of microplates, accidental jolts and other large accelerations due to mishandling are common. The resulting corruption of the experiment often necessitates that it be repeated.

Finally, once they are filled with solutions, current plates cannot be easily transported, e.g., between nearby buildings, or in a car or airplane from a home laboratory to another laboratory or to a synchrotron X-ray source. Current plates cannot be shipped by mail or private courier from one location to another. Plate tilting and impulsive accelerations during shipping and handling cause liquids contained in each well to spill out. This can disperse the liquid, increasing its total surface area, which can have a large impact on the rate of vapor diffusion between liquids in each well, on the rates of crystal nucleation and growth, and on the protein/biomolecule oxidation, degradation and/or crystal nucleation that occur at air-liquid interfaces. Plate tilting and impulsive accelerations can also cause mixing of solutions in wells contained within a given cell, corrupting the experiment. In protein crystallography, a growing fraction of X-ray data collection is performed remotely. Crystals mounted in special holders are frozen to near T=77 K and shipped to synchrotron sources for measurements. Shipping of crystallization microplates to synchrotrons for remote data collection is not currently feasible.

In addition to the above problems, current microplates for crystallization suffer from an additional problem. When liquid is dispensed into the reservoir well, it typically does not fill the well uniformly, especially if the well is much longer in one direction than another. The detailed behavior depends on how the aqueous solution wets the plastic or other material used to form the well, i.e., on the contact angle and contact angle hysteresis. If the contact angle is large, the liquid may "ball up", residing in the center of the well and avoiding its corners. It may be drawn to and wet a corner the well. If the contact angle is small (as for solutions containing alcohols) it may climb up the sides of the well. In all cases, this tends to reduce the total volume of liquid that can be easily dispensed into a well of given dimensions without overflow, and without the fluid contacting the top sealing film during the sealing of the plate. It also results in irreproducible liquid-air interface areas for the same liquid volume. Since the exposed surface area affects the rate of evaporation from the surface, this may affect the rate of vapor diffusion between wells and thus contribute to irreproducibility in crystallization.

Incomplete filling of reservoir wells also necessitates the use of wells that are much deeper or taller than necessary. Since the minimum thickness of a microplate is determined by the reservoir well height/depth, this in turn limits the minimum plate thickness. Minimizing plate thickness is desirable to minimize storage requirements for microplates. It is also desirable to facilitate X-ray inspection on commercial X-ray crystallography apparatus and at synchrotron X-ray sources, since the available space for a plate in these set-ups is typically quite constrained.

None of the currently available crystallization microplates include features that address these problems.

The present invention teaches devices and methods for manual and high-throughput protein crystal growth and growth of other biological and organic crystals, as well as for other applications in biotechnology. In one embodiment, a microplate comprises a plurality of cells, and a frame that defines the cells in the microplate. In each cell there is at least one well open at top. Each well in a cell may be enclosed at bottom, or it may be open at bottom, in which case the well bottom may be sealed by a separate part, which may be, e.g., a separate film or plate (e.g., of plastic, glass or metal) or a molded part. Current microplates for protein crystallization typically contain between 2 and 4 wells per cell.

The present invention provides means for allowing vapor communication between wells in the same cell while inhibiting liquid transfer between the wells. This means for vapor communication also allows some control over the rate of vapor transfer and equilibration between wells.

The present invention provides means for encouraging liquid drop spreading and complete and more uniform filling of a well to a given height, for liquids with a variety of surface tensions and contact angles.

The present invention thus provides means for maximizing liquid volume in a given well area, and thus for minimizing the well height required to hold a given volume in a given area. This allows the plate height to be minimized. Storage requirements for plates can then be reduced.

In microplates where one or more well bottoms or bottom sealing films are X-ray transparent, the smaller plate height allowed by the present invention allows incident and transmitted X-ray diffraction angles over a larger angular range without X-rays intercepting microplate materials.

The smaller well height also maximizes the range of harvest angles from which crystals or other samples can be retrieved from drops placed in a well whose bottom coincides with the bottom surface of the plate.

The present invention also prevents liquid from climbing up the side wall of a well to the top of the well wall. This makes sealing the top surface of the plate more reliable and secure.

The present invention provides means for inhibiting liquid motion and liquid contact of a top sealing surface when the plate is tilted, inverted or accelerated. This in turn allows the plate to be inverted for hanging drop crystallization, to be more roughly handled, and to be transported without mixing of solutions within the plate.

The present invention allows these features to be achieved while providing easy filling of all wells using standard liquid handlers and pipetters, and with dispensing patterns similar those used to fill existing commercial plates.

The wells within each cell are connected by communication channels on the top surface of the microplate. The cross-sectional areas of these channels are sufficiently small that, when at least one of the wells is filled with fluid, the hydrostatic fluid pressure created when the microplate is rotated to any orientation is insufficient to drive fluid flow through the channels from one well to the other. The communication channels are also sufficiently small that liquid splashing and fluid pressures generated within a well during routine handling or typical mishandling do not drive appreciable fluid flow through the channels. The channels may be straight. They may also be curved. They may have projections, barriers or offsets that prevent ballistic liquid motion through them. The invention is further comprised of a liquid retention ledge or ridge or aperture that extends around the interior perimeter of one or more of the wells, and projects outward from the wall of the well toward the well center. The open area of the aperture has a diameter that is smaller than the well diameter but is of sufficient length and width to allow standard diameter/profile pipette tips and other liquid dispensing tips to be inserted into the well and to contact the bottom of the well.

During liquid dispensing and well filling, liquid wetting to the lower surface of the ledge and contact line pinning by the interior perimeter of the aperture formed by the ledge facilitates spreading of the liquid across the bottom of the well and uniform filling of the well.

Without the ledge, a liquid with a contact angle near 90 degrees (typical of alcohol-free aqueous solutions on plastics) will tend to form a hemispherical drop on the bottom of the well. This drop will fill only a fraction of the well volume—especially for wells that are rectangular or elliptical—and will project upward close to the top surface of the well, where it may contact the film used to seal it. Any such contact can prevent proper sealing of the film to the top surface of the plate, and must be eliminated.

With the ledge, as liquid is dispensed the hemispherical liquid drop grows in height until it contacts the bottom surface of the ledge. Liquid then spreads laterally beneath the ledge, more uniformly filling the volume below the ledge, before eventually emerging through the aperture when the well is overfilled. For high surface tension liquids like water and salt-containing aqueous buffer solutions, the total liquid volume that can be dispensed in a well of a given height and base area can then be maximized.

The height of the wells is an important parameter in microplate design. The well height limits the minimum plate height, and thus determines plate storage volume requirements. Small well heights make it easier to dispense liquid into the bottom of a well and to retrieve, e.g., crystals that may grow in drops dispensed on the bottom of a well. They also increase the range of possible incident and diffracted X-ray beam angles that do not intercept plate materials during in situ X-ray inspection of well contents. Ledges/apertures as described here allow the liquid volume that can be dispensed in a given well volume to be increased, and thus allow the well height for a given liquid volume to be reduced.

When the well is filled until the liquid touches the bottom surface of the ledge, liquid then spreads across the aperture. The surface area of the liquid in the well that is exposed to the air above is thus defined by the aperture, rather than by the larger and otherwise irreproducible drop shapes typically formed by dispensed liquids. This may lead to more reproducible equilibration between wells and more reproducible crystallization outcomes.

Wetting and contact line pinning at the aperture's inner surface, and near complete filling of the volume below the ledge with liquid strongly inhibit liquid flow through the aperture and out of the well when the microplate is tilted or accelerated. Liquid flow out the aperture requires that air enter through it, which is strongly inhibited by the small aperture dimensions and the liquid surface tension. Positioning the top surface of the ledge/aperture a finite distance below the microplate's top surface prevents any liquid that bulges through the aperture during tilting, inverting and acceleration from contacting the top sealing film and spreading. Together, the combination of the retaining ledge/aperture within a well and communication channels connecting the wells strongly inhibit liquid transfer between wells. This allows the microplates to be rotated to any orientation without liquid transfer, to survive routine handling and mishandling, and to be transported and shipped without liquid transfer.

The retaining ledge/aperture and the communication channels thus allow microplates to be produced that have additional functionality and allow new methods for using microplates.

FIGS. 1 (a) and (b) show top and side views of a 96 cell microplate used in protein crystallization, manufactured by Swissci. FIG. 1 (c) shows a schematic of one cell in such a microplate with a small protein drop well at left and a much larger reservoir solution well at right.

FIG. 2 (a) shows a top view of a microplate in one embodiment of the present invention. FIGS. 2 (b) and (c) show top and cross-sectional side views of a single cell of a microplate in this embodiment, with communication channels 17, liquid retention aperture 15 and liquid retention ledge 16.

FIG. 3 shows example alternative embodiments of the communication channels that connect wells within a single cell according to the present invention.

FIGS. 4 (a) and (c) shows side schematic views of two alternative embodiments of a well with a liquid retention ledge and aperture according to the present invention. FIGS. 4 (b) and (d) show fully rendered views of cells in a microplate, with the right-hand well in each cell having liquid retention ledges; the bottom of the wells are sealed using a separate part which may be a film, a plate, or a separately molded part. FIG. 4 (e) shows a microplate similar to 4(b) but with an integral sealed bottom for each well. FIGS. 4(f) and 4(g) show variants of 4(e) in which the left-hand well depth is smaller than the right-hand well depth.

FIG. 5 (a) schematically shows how water spreads during filling of a well in a conventional microplate. FIG. 5(b) shows how water spreads during filling of a well with a liquid retention ledge and aperture, according to one embodiment of the present invention.

FIG. 6 (b) shows photographic images of water spreading during filling of a microplate with a liquid retention ledge and aperture, in one embodiment of the present invention

The present invention consists of modifications to microplates such as those used in protein crystallization and screening that strongly inhibit the transfer of liquid between wells within each cell of the microplate while allowing vapor communication between the wells. This allows the microplates to be used in any orientation and to be handled, transported and shipped without mixing of liquids in the connected wells. This also allows the reservoir well volume and height to be minimized, and also increases the consistency of reservoir fluid surface area.

Vapor Communication Channels.

Figure 1:
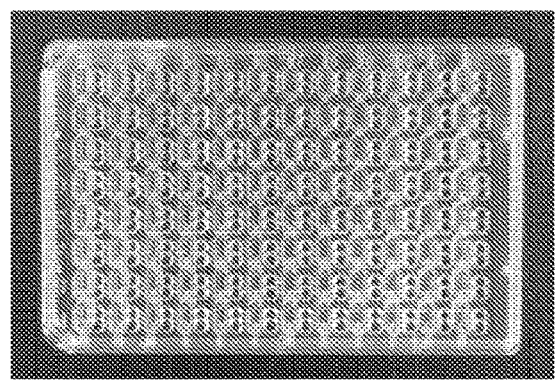
Figure 1:
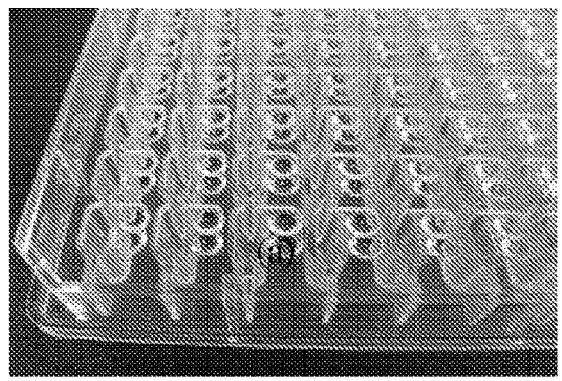
Figure 1:
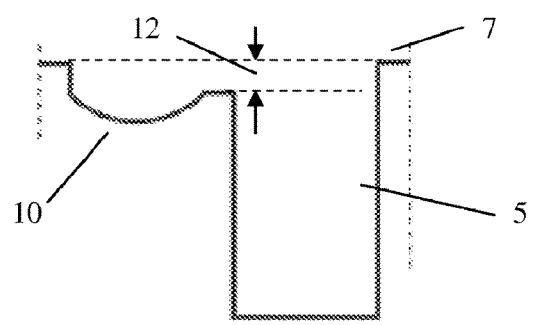

As illustrated in FIG. 1, in current crystallization microplates, within each cell the wells for reservoir solution 5 and for protein drops 10 are open to each other, allowing free exchange of vapor between the reservoir well and the protein well(s). This is accomplished by leaving a gap 12 between the top of the barrier or wall between wells and the top surface 7 of the microplate, as shown in FIG. 1(c), the top surface being sealed after microplate loading using a plastic film. Typical dimensions of this gap are approximately 1 mm high by 8 mm wide. This large gap allows liquid to easily flow between wells when the microplate is tilted, inverted or bumped.

Figure 2:
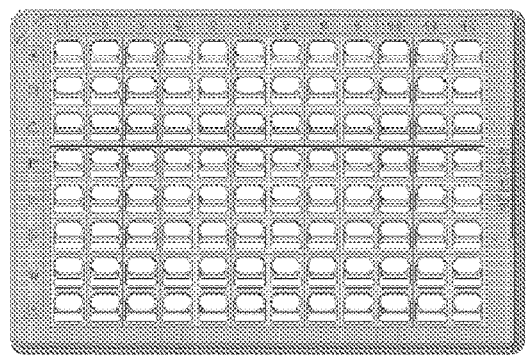
Figure 2:
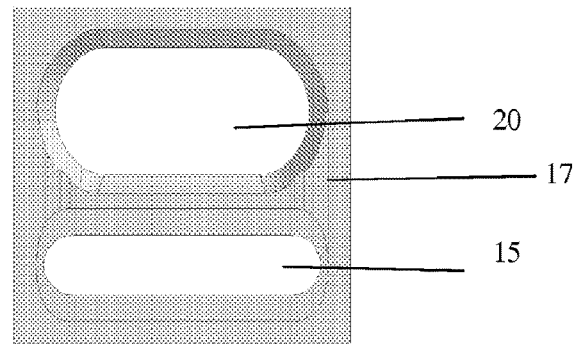
Figure 2:
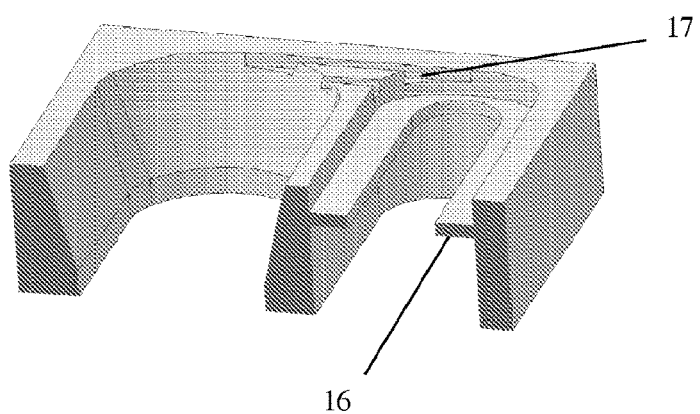
Figure 3:
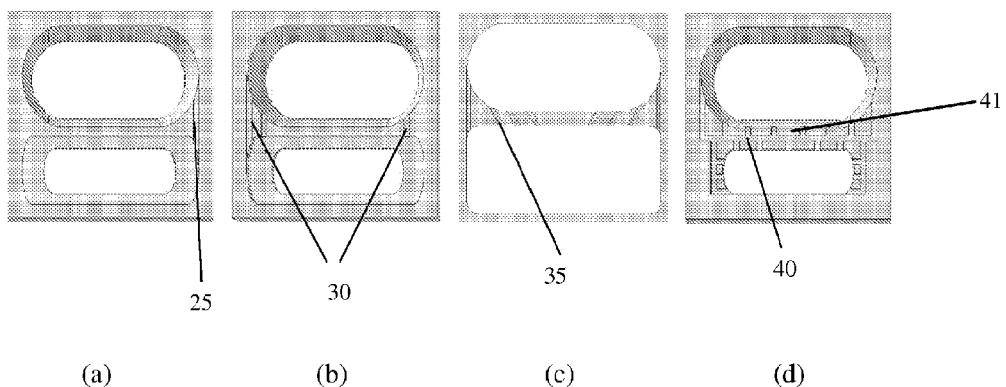
Figure 4:
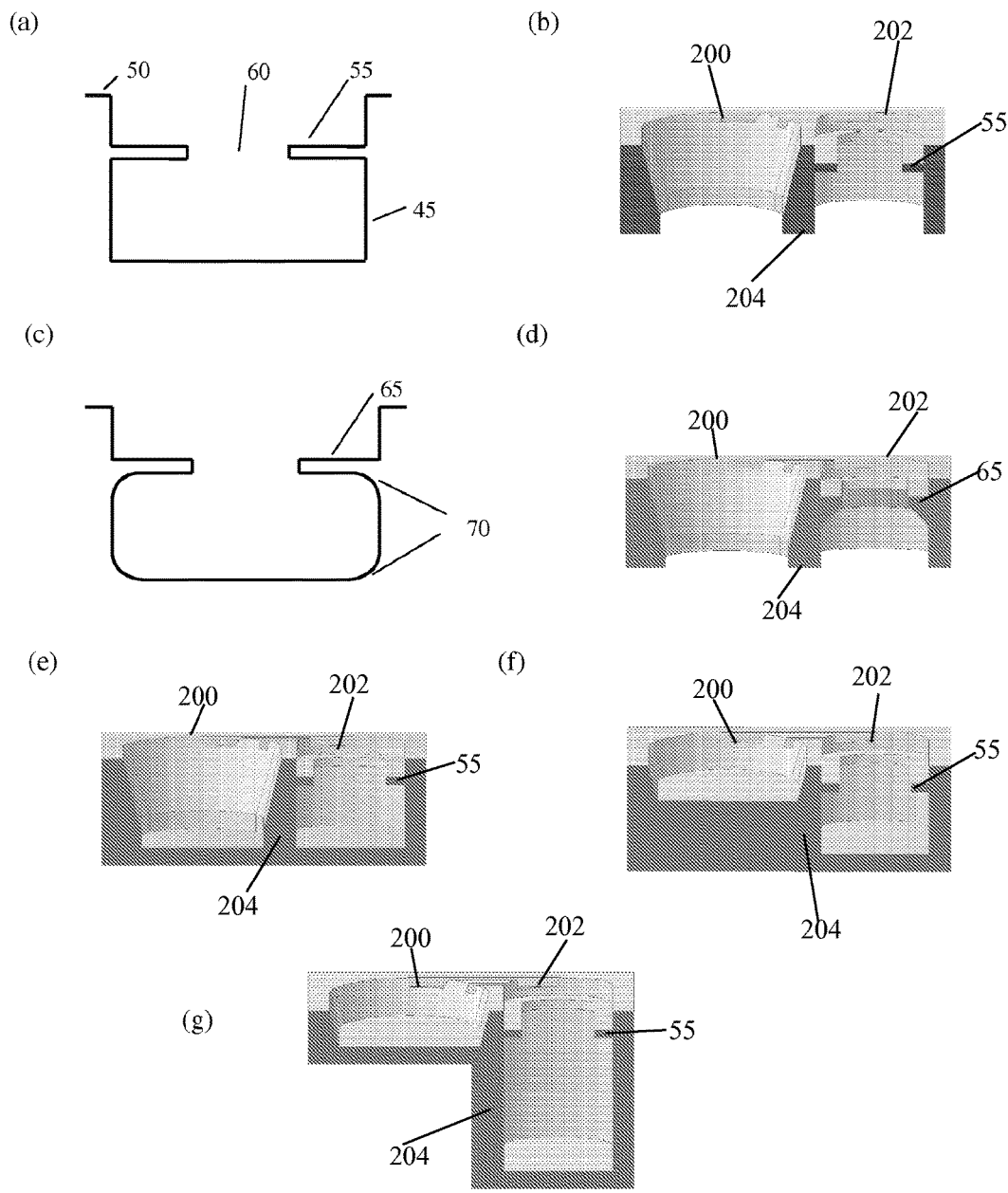

Various approaches could reduce liquid transfer while allowing vapor communication between wells. For example, a barrier of micro porous material (e.g., filter material) could be used to fill the gap between the top of the barrier wall and the top surface of the microplate. Our preferred embodiments, schematically illustrated in FIG. 2, involve extending the top of the barrier wall between protein drop well 20 and reservoir well 15 within a given cell to the top of the microplate, and forming small-cross-sectional area communication channels 17 in the top surface of the plate, which provides the sealing surface of the cell. FIG. 3 illustrates alternative embodiments of the channels. In FIG. 3(a), there is a single communication channel 25 disposed at one end of the reservoir well, so that any liquid transfer that does occur between wells occurs away from the drops which may be disposed near the center of the adjacent well. There may be more than one communication channel 30 (FIG. 3(b)), and the channels 35 can be angled (FIG. 3(c)) to direct any fluid that does enter the channel away from drops in the adjacent well. The communication channels 40 can have projections, barriers, offsets or notches 41 and can be redirected around the barriers 41 etc. (FIG. 3(d)) to, for example, inhibit ballistic motion of fluid during impulsive accelerations.

The dimensions, shape and location of these channels determine their effectiveness in allowing vapor communication while inhibiting or preventing liquid transfer.

When a microplate with communication channels is tilted from the horizontal so that liquid flows into contact with the communication channel openings on one side of the barrier wall, the hydrostatic pressure in the liquid as well as the pressure associated with surface tension forces will drive any liquid motion through the communication channel. For continuous flow of aqueous solutions in small channels, the Reynold's number is small and the flow is viscous. The volume flow rate is then related to the pressure difference $\Delta p$, the channel radius $r$ (for an approximately circular cross-section channel), the channel length $L$ and the fluid viscosity $\eta$ by $Q=\pi r^4 \Delta p/8\eta L$ and the average flow velocity is $v_{av}=r^2\Delta p/8\eta L$. Assuming $\eta=8.9\times10^{-4}$ Pa s (pure water) and typical values appropriate for 96 well SBS standard crystallization microplates of $L\sim1$ mm, $\Delta p_{hydrostatic} \sim \rho g h \sim 50$ Pa (with h=0.5 cm, a typical well height). With r~75 micrometers (a feature size that can be conveniently injection molded), the average flow velocity is then ~4 cm/s and the flow rate is ~0.7 μl/s. In the case of a microplate that is accelerated with acceleration a rather than tilted, the maximum $\Delta p \sim \rho a h$, so for a>>g the flow rates can be larger. If the acceleration is transient (e.g., due to a bump), the total flow can be small even if a is large. The viscosity of air, $1.78\times10^{-5}$ Pa s, is 50 times smaller than that of water, so flow rates for a given pressure difference are much larger.

A second and, for reducing liquid transfer between wells, more important effect is the pinning of liquid contact lines by solid surfaces. The contact angle $\theta$ formed by the air-liquid interface at a solid surface is determined by the properties of the liquid and surface. In a channel or tube, this leads to the formation of a curved liquid meniscus. For a meniscus with a given contact angle $\theta$, the pressure difference between the liquid and the air on the other side of the meniscus is $\Delta p=2\gamma \cos(\theta)/r$, where $\gamma$ is the liquid surface tension and r is the radius of the channel or tube. The liquid contact line and the meniscus will remain pinned for some range of values $\theta$ between $\theta_{min}$ and $\theta_{max}$; the difference between these extreme angles is the contact angle hysteresis, and is determined by the wall roughness, among other factors. This contact angle hysteresis is the analog of static friction for a liquid contact line. Consequently, a minimum pressure in the liquid is required to induce flow through the channel or tube, given by $\Delta p_{min}=2\gamma \cos(\theta_{max})/r$. Using a typical $\theta_{max} \sim 140°$, $\gamma=0.0728$ N/m (water) and r=75 micrometers gives $\Delta p_{min}=1500$ Pa. Thus, for sufficiently small channels, the pressure difference required to produce flow will be larger than the hydrostatic pressure difference generated when the microplate is tilted or inverted. For 150 micrometer wide channels, it will be roughly 30 times larger, suggesting that microplate accelerations up to ~30 g will not cause fluid motion.

Experiments have been performed on 96 well SBS standard microplate prototypes with rectangular and trapezoidal cross-section communication channels. Channel dimensions ranged from 0.5 by 0.25 millimeters to 0.25 by 0.075 millimeters. Wells were roughly 4 mm deep. In all cases, even when the reservoir well was completely filled with liquid, no liquid transfer occurred when the microplates were tilted to any orientation, consistent with the above calculations. Communication channels of these dimensions had only small effects on the rate at which vapor pressure equilibration occurred between solutions in wells separated by these channels; this equilibration rate is determined primarily by the rate of evaporation from the liquid surface, which depends on its surface area exposed to air. Since accelerations during mishandling (e.g., dropping the plate) are transient, any liquid volume that is transferred between wells tends to be extremely small. This transfer can be inhibited to some extent by placing a small barrier or "splash guard" in front of the entrance and exit of the communication channels; and by extending the length of the channel by curving, bending or redirecting it around barriers. Excess pressure developed during accelerations must first drive flow through the entire length of the channel. If the communication channel width is small enough and the path long enough, the liquid will not reach the other well during the duration of the acceleration and associated excess pressure. However, repeated large accelerations may eventually drive very small amounts of fluid out of the communication channel and into the adjacent well.

In addition to minimizing liquid transfer volumes, appropriately arranged communication channels can also minimize the effects of small liquid transfers, especially those occurring due to rough handling and impulsive forces. For example, the channels can be arranged so that any liquid that flows into them from the reservoir well and then out of them to the protein/adjacent well is unlikely to contact the protein drops on the bottom of the well. This can be accomplished by directing the communication channel outlets away from the drops. For example, as shown in FIG. 3 (a-c), when the protein drops are disposed away from the ends of the well, the channels can be disposed at either end and directed away from the protein drops. Guards placed at the outlet of the channel can be used to deflect liquid down the sides of the well wall.

Vapor communication channels can also provide some control over the rate of vapor transfer and vapor equilibration between connected wells. The rate of transfer of volatile components of the liquids in the wells—including water and alcohols—depends upon the rate of evaporation per unit area from the liquid-air interface, the surface area of liquid-air interface, and the rate of vapor diffusion and convection. The communication channels affect vapor diffusion, by constricting the area through which diffusion occurs, and vapor convection, since convection within the channels is strongly suppressed in sufficiently small channels, e.g., those of the prototypes described above. The modulation of the net rate of transfer of volatile components between wells is determined by which process—evaporation from the liquid surface, convective and diffusive transport within each well, or diffusive transport through the channel—is slowest. For highly volatile components like alcohols, the effects of the channels may be dominant, but for slowly evaporating solutions like aqueous buffer containing 30% polyethylene glycol, the evaporation rate may be limiting. In any case, reducing the channel cross-section dimensions and increasing their length should eventually make transport through the channel the limiting step. The channel dimensions and the total number of channels can then be used to control—specifically, to reduce relative to the large-area channel limit—the rate of vapor transport and equilibration between wells. Filling the channels with an oil or other non-volatile material could be used to further reduce diffusion through the channel and thus to further reduce the rate of vapor equilibration. In protein crystallization, slower equilibration is often desirable, as it can produce less nucleation and larger crystals.

Liquid Retention Ledge/Apertures

As shown in FIG. 4(a)-(d), in its simplest form, the liquid retention ledge/aperture is formed by a ledge 55 that projects outward from the walls 45 of the well (which has a top surface 50), at some position between the bottom and top of the well. The parameters of this ledge are its thickness, the ratio of this thickness to the well depth, the dimensions of its inner aperture 60 (or the amount by which the ledge projects outward from the well wall) and its height above the bottom of the well. First well 200, second well 202, and separation wall are also shown. The ledge can be tilted upward or downward. It may have a rectangular cross-section (FIGS. 4(a) and (b)). It may instead have a bottom surface that, e.g., curves to meet with the wall (FIGS. 4(c) and (d)). It may have projecting or raised lips immediately adjacent to the aperture to control contact line pinning there. There may be more than one aperture in a given well. The shape and size of the aperture formed by the ledge should be optimized to prevent liquid motion through the aperture when the plate is tilted, inverted or roughly handled, and should also allow easy filling using standard liquid handlers and pipetters. The well bottoms may be open—to be sealed by a separate part—as in FIGS. 4(b) and (d); or one or all wells within a cell may have an enclosed bottom, as in FIG. 4 (e-g). The wells within a cell may have the same depth (FIGS. 4(b) and (d)), or they may have different depths (FIG. 4(e-g)).

Current 96 cell microplates for protein crystallization have reservoir well volumes of roughly 40 to 200 microliters. Since most plates conform to the SBS dimensions, well volumes decrease with the number of cells in the plate. With low-water vapor permeability plastics such as cyclic olefin copolymer (COC), well volumes can be reduced to approximately 10 microliters for experiments lasting one month, and to smaller volumes for shorter experiments, without appreciable effects due to water loss from the cells.

Figure 5:
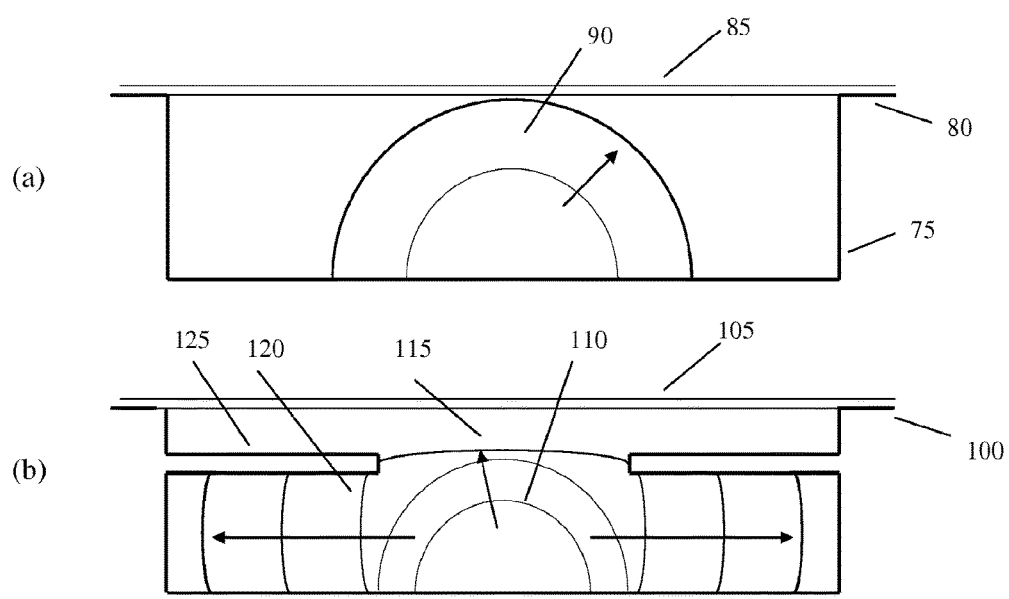
Figure 6:
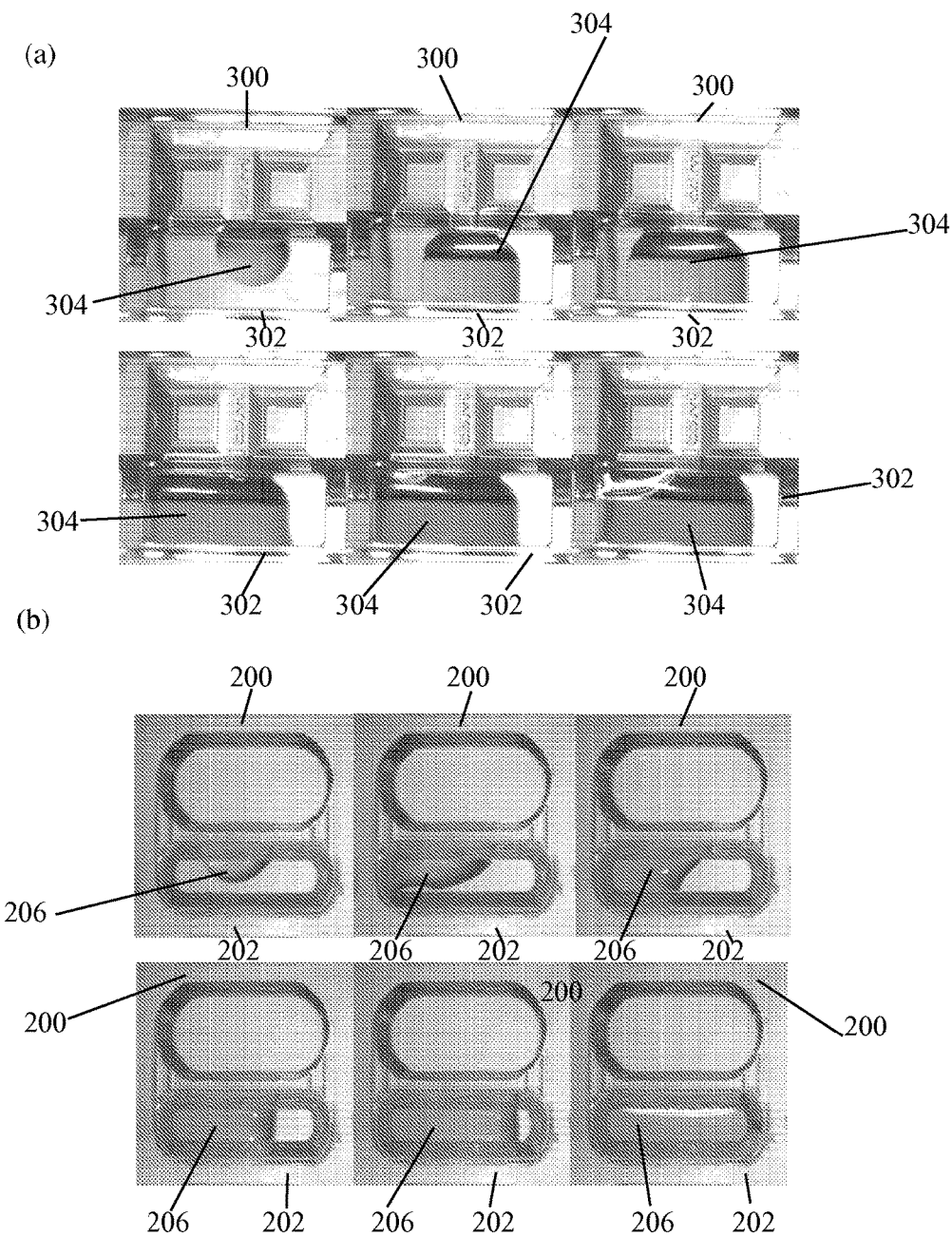
FIG. 6 (a) shows photographic images of water spreading during well filling of a standard commercial microplate.

The plastics used in conventional injection molded microplates tend to be somewhat hydrophobic. As illustrated in FIG. 5(a), when aqueous solutions are dispensed into conventional flat or curved bottom wells, they tend to form hemispherical domes 90 on the bottom of the well 75 rather than wet and spread uniformly throughout the well. The liquid may reside only near the center of the typically rectangular or elongated wells, or it may be drawn to a corner. Consequently, for fixed volume the exposed surface area of the liquid will vary, changing the rate of equilibration of the liquids in each well. This also makes it more difficult to completely fill a well without it overflowing, or without having liquid touch the top sealing film 85 when the plate is sealed. FIG. 6(a) shows a sequence of images acquired during filling of the reservoir well of a commercial protein crystallization microplate. As liquid is added, the liquid often accumulates in one side of the well, and the liquid level rises to the top of the well on that side, before the liquid finally spreads across the entire bottom of the well. Fully filling the well is usually impossible without having liquid contact the top sealing surface, which can prevent plate sealing. If the sealing film is not applied, when the plate is tilted to 90 degrees or inverted, most or all of the liquid will flow out of the well. With the top sealing film applied, tilting or inversion will typically result in substantial liquid transfer between wells.

As illustrated in FIG. 5(b), by adding the liquid retention ledge 125 and aperture 115, as liquid is injected into the well, the liquid's top surface 110 eventually contacts and wets the bottom surface of the retention ledge. The liquid then spreads laterally (120) beneath the ledge as additional liquid is added. Surface tension forces prevent spreading of the liquid through and out the aperture, so the liquid will then expand laterally beneath the ledge until the volume beneath the ledge is nearly completely filled (arrows).

The minimum outward projection of the ledges from the well wall required to keep liquid from rising to the top surface of the plate (and contacting the sealing film) depends on the shape of the liquid drop formed on the bottom of the well during filling, on the ratio of the well depth to well width, on the vertical position of the ledge relative to the bottom of the well, and also on how the plate is filled. The drop shape depends on its volume, surface tension and contact angle at the well bottom. For a small depth to width ratio and/or for a ledge placement near the top of the well as in FIG. 5(b), the ledge must be relatively wide, whereas for a large depth to width ratio or for ledge placement closer to the bottom of the well, the ledge can be relatively small. For rectangular or otherwise elongated wells, the ledge width can be reduced at the narrower ends of the wells relative to on the wider sides of the wells, as the ledges on the wider sides will largely determine liquid retention. If the liquid is not dispensed in the center of the well but is dispensed toward one side, the ledge projection can be reduced and still effectively contain the liquid.

Experiments using prototype 96 cell microplates have confirmed that liquid retention ledges cause liquid spreading and more uniform well filling for water and variety of aqueous solutions and mixtures ("screens") containing alcohols, ethylene and polyethylene glycols, glycerol, salts, detergents and other organic compounds commonly used in protein crystallization. FIG. 6(a) shows a sequence of images as liquid is added to a conventional well on a commercial 96 cell plate. The liquid spreads and then rises to the top surface of the plate at the left end of the plate (so that it will contact the sealing film when the plate is sealed) before continuing to spread to the right end. When the plate is tilted, the liquid freely flows out of the well. A first well 300, a second well 302, and liquid (a water droplet) 304 is shown in FIG. 6(a). FIG. 6(b) shows a corresponding sequence of images in a prototype plate according to the present invention. A first well 200, a second well 202 and liquid (a water droplet) 206 is shown. As liquid is added, the liquid quickly contacts the bottom surface of the ledge, and then spreads uniformly beneath the ledge until the entire volume below the ledge (with the possible exception of a small bubble) is filled. Even with the sealing film not applied, the plate can be tilted to any orientation or inverted without liquid flow out of the well through the aperture. Using the well dimensions of FIG. 6(b), experiments with ledges of varying widths/extensions from the well sidewall suggest that the utility of the ledges in promoting liquid spreading and more uniform well filling is largely insensitive to ledge width, for widths of at least 0.2 mm.

Figure 7:
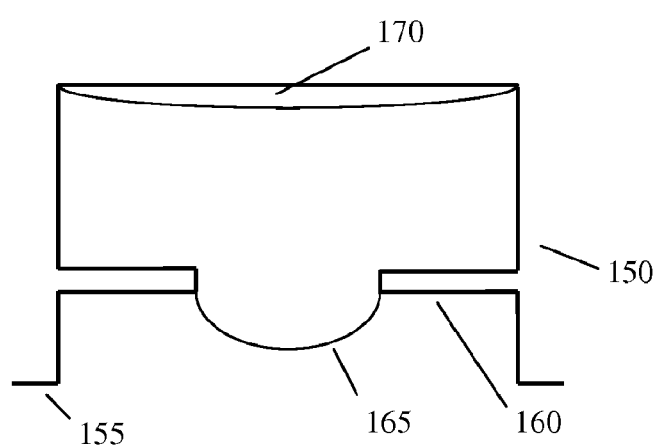
FIG. 7 shows one liquid-containing well in one embodiment of the present invention, when it is inverted.

When the microplate is tilted or inverted, the liquid retention ledge/aperture inhibits liquid flow out though the aperture by several mechanisms. First, as shown in FIG. 7, as the liquid 165 begins to bulge through the aperture formed by ledge 160, it must increase its surface area and so there is surface-tension-related pressure that opposes this bulging. This opposing pressure increases with the amount of bulge to a maximum given roughly by $p_{max}=2\gamma \cos \theta_{max}/r$ where $\gamma$ is the surface tension of the liquid-air interface, r is the aperture radius, and $\theta_{max}$ is the maximum stable contact angle of the liquid-air interface relative to the top surface of the aperture. This pressure (roughly 150 Pa for water in a 1 mm radius aperture), can exceed the hydrostatic pressure in the liquid in a shallow well, and prevent it from moving. In order to obtain maximum benefit from this effect, the top sealing surface 155 of the microplate must be far enough away so that liquid bulging through the aperture does not contact the sealing film sealing this top surface when, e.g., the plate is inverted after filling.

Second, the liquid is incompressible. Thus, as the liquid displaces into and then bulges out of the aperture, the gas volume in the unfilled space 170 on the "filled" side of the aperture must increase, producing a decrease in pressure in that space that opposes the motion. If the initial gas volume is very small, the pressure drop for even small displacements may be large. For example, if the unfilled volume below the aperture in a 40 microliter well is microliters (10%), the formation of a 1 millimeter diameter hemispherical liquid bulge through the aperture produces a pressure drop of 6500 Pa, or roughly 130 times larger than hydrostatic pressure.

Several design features can increase the filled volume fraction occupied by the incompressible liquid below the liquid retention ring and minimize the unfilled volume fraction occupied by compressible air. The well can be made more nearly square or circular, as viewed from above. The corners 70 of the well can be rounded (FIGS. 4(c) and (d)) to reduce trapping of air bubbles there, especially below the bottom surface of the ledge.

Figure 8:
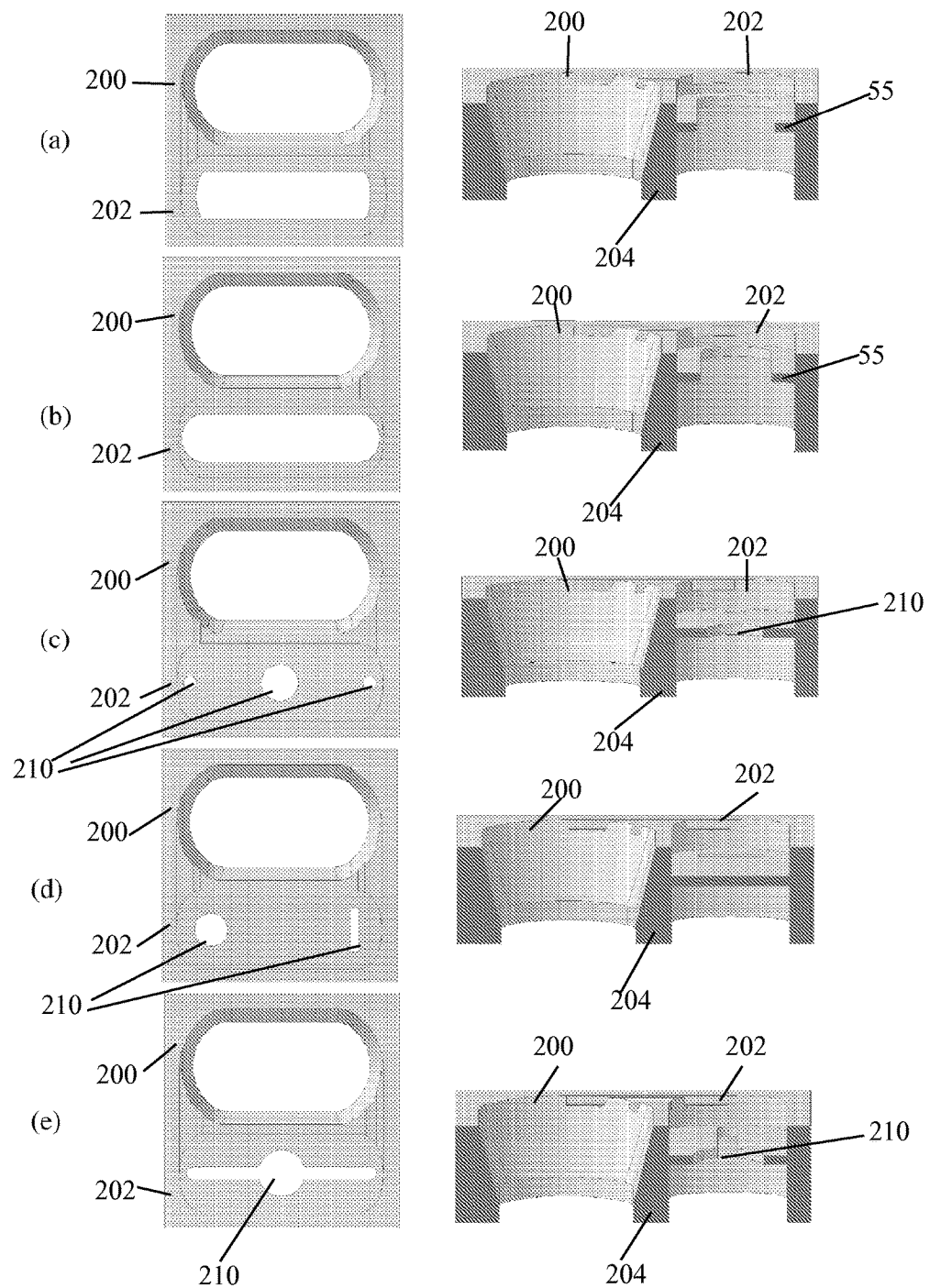
FIG. 8 shows alternative embodiments of the liquid retention ledge and aperture in a well of a microplate according to the present invention.

FIGS. 8(a)-(e) show a first well 200, a second well 202, a ledge 55, a separation wall 204 and apertures 210. Wider ledges tend to trap air beneath the ledge at either end of a rectangular well. This trapping can be reduced by reducing the width of the ledge. For rectangular or otherwise elongated wells, the width can be reduced only at the well ends (FIG. 8(b)), minimizing air trapping while minimizing the width of the aperture. Small diameter (e.g., 150 micrometer) "vent" apertures can be disposed in the ledge at either end of the well, allowing air to escape through them during filling from the center. The ledge can be then be extended to form a continuous sheet across the well, with holes for filling and venting (FIG. 8(c)). The filling aperture can be disposed at one end of the well and a single vent aperture at the other end (FIG. 8(d)). The filling aperture can be disposed in the middle, and thin slits extended from either side of it as in FIG. 8(e) to allow gas escape during filling but to minimize fluid motion out compared with, e.g., the apertures in FIGS. 8(a) and (b) during handling and acceleration. Third, in order for liquid to flow out of the aperture during, e.g., microplate rotation to a vertical or inverted orientation, air must flow in through it. If the well below the aperture is filled, the aperture will remain covered by liquid during rotation, so an air bubble must form and move through the aperture in order for liquid to flow out. Because of the large pressure increase that inhibits uniform liquid motion out of the aperture, this may involve creating an outward-protruding bubble in part of the aperture and an inward-protruding bubble in another part. The surface-tension-related pressures required to create these bubbles are inversely proportional to the bubble diameter. Consequently, any tendency for these bubbles to form can be suppressed by making the aperture as small as is feasible in all its dimensions. The smallest dimension is limited by the size of the dispensing tips in commercial liquid handlers and pipetters, and by the precision and accuracy in positioning the tips relative to the plate. In FIG. 8(c), a central aperture is provided for liquid filling and two much smaller vent apertures at either end of the well allow air escape during filling.

Finally, any liquid motion and especially the bubble formation described above occur on a timescale that is determined by the liquid's viscosity. This viscosity thus inhibits bubble formation and liquid flow out of the aperture in response to impulsive and other short-duration perturbations.

Experiments on microplate prototypes with 3-4 mm deep reservoir wells and liquid retention ledges/apertures filled with volumes between 20 and 40 microliters show that the ledges/apertures prevent all liquid motion out of the well during ordinary manual plate handling, during rotations and inversions, and when the microplate is held for extended periods in vertical and inverted orientations, including when there is no top film sealing the well. This contrasts with the behavior of liquid in prototype wells without ledges (as are used in current microplates), where liquid easily flows out of the reservoir and mixes when the plate is tilted or inverted. Liquid only flows out through the aperture when the plate experiences intense impulsive forces, e.g., those that occur if the plate is dropped from a height of, e.g., two feet onto a hard surface In our experiments, we have used wells with liquid retention ledges that produce apertures of width 2 mm— determined by the ~1 mm typical size of liquid dispensing pipette tips and tolerances in microplate positioning relative to the dispensing tip. Experiments using ledges placed at varying distances below the top surface of the microplate showed that a distance of approximately 0.5 mm gave good results with no tendency for liquid to contact and spread on the top sealing surface for wells 3-4 mm deep. Smaller apertures can be used to increase inhibition of flow during acceleration, but place constraints on the kinds of liquid dispensing tips that can be used to fill the plate and the accuracy of the plate positioning relative to the dispensing tips. Injection molding the liquid retention ledge is difficult if the bottom of the well is also injection molded in the same step—as is the case with all commercial microplates currently sold for protein crystallization. A simpler approach is to seal the well bottom after molding with a separate plastic film or plate or molded part. Molding and release from the mold is then straightforward, lowering cost.

Plates Combining Vapor Communication Channels and Liquid Retention Ledges.

Experiments on 96 well plate prototypes with liquid retention ledges/apertures and 150 micrometer wide communication channels (with cells as shown in FIG. 4(b)) show that, when the reservoirs filled with roughly 40 microliters of water (high surface tension) or 30% isopropanol in water (low surface tension) are placed in a single standard bubble bag, they can be dropped from a height of six feet onto a concrete floor with little transfer of liquid between the reservoir wells and the protein drop wells.

Microplate Storage and Shipping Assembly/System.

In some applications, it is desirable to be able to ship microplates between laboratories by conventional mail or courier service. For example, it is desirable to ship plates from university or industrial laboratories to synchrotron X-ray sources for X-ray inspection. This shipping requires that (1) variations in average temperature be minimized to prevent freezing, precipitation and other effects that may damage the samples in the plate; (2) temperature gradients across the plate be minimized to prevent evaporation and condensation; and (3) peak accelerations be minimized to minimize liquid transfer between wells. (1) and (2) can be achieved using standard commercial shipping containers, such as those comprised of insulating Styrofoam boxes with high heat capacity gel packs inside to maintain temperature. (3) can be achieved using bubble wrap, air pillows, foam or other materials that compress during impact and that have an inelastic (dissipative) response to compression, so as to reduce peak accelerations and thus peak forces exerted on objects contained within them. A commercial microplate system for, e.g., protein crystallization, shipping and X-ray inspection may then comprise a microplate with liquid retention ledges/apertures and narrow vapor communication channels; a cardboard box lined with shock-absorbing foam; an interior thermally insulating Styrofoam container; high heat capacity gel packs; and additional foam or bubble packaging to further reduce accelerations of plates inside the Styrofoam container.

During shipping, microplates may also experience reduced ambient pressures. Microplate prototypes with vapor communication channels and liquid retention ledges, and that had both top and bottom surfaces sealed using separate polymer films, were tested in a chamber with an air pressure of 22.2 inches of Hg (75 kPa or roughly ¾ of sea level atmospheric pressure). This pressure corresponds to the minimum pressure in the cargo hold of a commercial airliner. These tests showed no transfer of liquid between wells or other problems after repeated cycling between reduced pressure and atmospheric pressure.

In standard use, the plate bottom is sealed, either during injection molding or by attachment of a separate film or plate or injection molded part. Reservoir liquid is dispensed using a manual pipetter or automated liquid handler through the liquid retaining aperture and into the well below, filling the well below the liquid retention ledge as completely as possible Protein solution is then dispensed as drops on the bottom surface of the adjacent protein well. The top surface of the microplate is then sealed using a vapor-impermeable sealing film. The plate is then rotated to a desired orientation (usually either its original horizontal orientation or an inverted orientation) for crystal growth. The plate is then rotated to another orientation (usually vertical) to examine the contents of each cell using X-rays, UV or visible light, or other probes. The plate may also be rotated to a vertical orientation immediately after filling, allowing vertical storage and inspection during the experiment. This may be preferable to storage in a horizontal orientation if a plate to be inspected in a vertical orientation multiple times during an experiment.

The description above has presented several alternative embodiments. The invention is not restricted to microplates for protein crystallization, or to microplates. It can be used in any kind of microplate. It can also be used in any kind of device where it is desirable to have vapor communication between two or more wells or chambers and easy filling and removal of material from wells from a top surface, while preventing liquid transfer between wells during microplate rotation or acceleration, and allowing device use in any orientation.

All references, including publications, patent applications, and patents cited herein are hereby incorporated by reference in their entireties to the extent allowed, and as if each reference was individually and specifically indicated to be incorporated by reference and was set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein is merely intended to serve as a shorthand method of referring individually to each separate value falling within the range, unless otherwise indicated herein, and each separate value is incorporated into the specification as if it was individually recited herein.

All methods described herein may be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

What is claimed is:

1. A microplate comprising:
    a frame comprising a substantially planar top surface extending in a first plane, a bottom surface extending in a second plane substantially parallel to the first plane, wherein the top surface and the bottom surface are connected and separated by at least one side surface extending in a third plane normal to the first plane and the second plane, and wherein the frame includes a plurality of cells formed therein, each cell comprising:
    a first well having a top surface extending in the first plane and a bottom surface extending in a second plane configured to contain between 10 and 200 microliters of stationary fluid;
    a second well having a top surface extending in the first plane separated from the first well by a predetermined width and configured to contain equal to or less than 10 microliters of stationary fluid;

wherein said first well and said second well are separated by a barrier wall extending in a first direction from the bottom surface to the top surface and extending in the first plane, and extending in a second direction along a longitudinal axis and the entire predetermined width between the first well and the second well;

wherein said first well and said second well are connected via at least one vapor communication conduit comprising at least one groove formed in the top surface of the barrier wall, wherein the groove is positioned between portions of the top surface of the barrier wall that extend in the first plane, and structured to allow vapor communication between said first well and said second well, and to facilitate the inhibition of liquid transfer between said first well and said second well when at least one cell contains a liquid and when said frame is tilted from a horizontal position to the vertical or is inverted or when said frame is subjected to impulsive accelerations; and wherein the top surface of said barrier wall comprises a center point and two end points, and wherein said at least one vapor communication conduit is positioned in the top surface of barrier wall (i) at a position between the center point and one of the two end points of the top surface of said barrier wall, (ii) at an angle to the longitudinal axis, or (iii) where the conduit follows a non-linear path from the first well to the second well such that there is no line-of-sight path through the path; and wherein when the microplate is held in the horizontal orientation the liquids in the first well and in the second well fill the wells to a level below the position of said at least one vapor communication conduit.

2. The microplate of claim 1, wherein said at least one conduit is located adjacent to one of the two end points of the top surface of said barrier wall.

3. The microplate of claim 1, wherein said at least one conduit is non-linear.

4. The microplate of claim 1, wherein said at least one conduit has a width of between about 0.075 millimeters to about 0.25 millimeters.

5. The microplate of claim 1, further comprising a plurality of conduits structured to allow vapor communication between said first well and said second well, and to facilitate the inhibition of liquid transfer between said first well and said second well when at least one cell contains a liquid and when said frame is tilted from a horizontal position to the vertical or is inverted or when said frame is subjected to impulsive accelerations, wherein each of which of said plurality of conduits is carved into the first top surface of said frame.

6. The microplate of claim 1, further comprising a liquid retention ledge that is connected to and extends around at least a portion of an interior perimeter of one of said first well and said second well at a predetermined distance below the top surface of the frame, and projects outward from the interior perimeter forming an aperture with a diameter that is smaller than a diameter of the interior of said one of said first well and said second well.

7. The microplate of claim 6, wherein said liquid retention ledge is structured to facilitate uniform filling of said one of said first well and said second well with liquid as liquid is added and to facilitate the prevention of the formation of air bubbles therein.

8. The microplate of claim 7, wherein said liquid retention ledge is structured to pin the liquid contact line when liquid is added to said one of said first well and said second well thereby facilitating the prevention of the liquid from rising above the level of the liquid retention ledge during the addition of the liquid.

9. The microplate of claim 8, wherein said liquid retention ledge projects outward at a distance of at least 0.2 millimeters from the interior perimeter of said one of said first well and said second well.

10. The microplate of claim 6, wherein said liquid retention ledge is structured to facilitate the prevention of liquid from flowing out of said one of said first well and said second well when said frame is tilted from a horizontal position or when said frame is subjected to impulsive accelerations.

11. The microplate of claim 10, wherein said liquid retention ledge comprises a rectangular cross-section.

12. The microplate of claim 10, wherein said liquid retention ledge comprises a curved bottom portion, wherein said curved bottom portion of said liquid retention ledge is structured to facilitate the prevention of air bubble trapping during filling of said one of said first well and said second well with liquid.

13. The microplate of claim 12, wherein said liquid retention ledge is structured to form a plurality of apertures.

14. The microplate of claim 13, wherein a first one of said plurality of apertures is formed adjacent to the interior perimeter of said one of said first well and said second well.

15. The microplate of claim 14, wherein a second one of said plurality of apertures is substantially centrally formed in said one of said first well and said second well.

16. The microplate of claim 15, wherein each of said first and said second one of said plurality of apertures is substantially circle-shaped.

17. The microplate of claim 16, wherein a diameter of said second one of said plurality of apertures is larger than the diameter of said first one of said plurality of apertures.

18. The microplate of claim 17, wherein said first one of said plurality of apertures has a diameter of about 150 micrometers.

19. The microplate of claim 6, wherein said one of said first well and said second well including said liquid retention ledge further comprises a bottom portion with rounded corners.

* * * * *